(12) United States Patent
Zepf

(10) Patent No.: US 8,414,610 B2
(45) Date of Patent: Apr. 9, 2013

(54) SURGICAL INSTRUMENT

(76) Inventor: Christoph Zepf, Dürbheim (DE)

( * ) Notice: Subject to any disclaimer, the term of this patent is extended or adjusted under 35 U.S.C. 154(b) by 551 days.

(21) Appl. No.: 12/611,392

(22) Filed: Nov. 3, 2009

(65) Prior Publication Data
US 2010/0114139 A1    May 6, 2010

(30) Foreign Application Priority Data

Nov. 14, 2008   (DE) .......................... 20 2008 015 151

(51) Int. Cl.
*A61B 17/32*        (2006.01)
(52) U.S. Cl. ...................................................... 606/184
(58) Field of Classification Search .......... 606/167–185; 604/22
See application file for complete search history.

(56) References Cited

U.S. PATENT DOCUMENTS 5,089,000 A * 2/1992 Agee et al. .................... 606/170
7,621,932 B2 11/2009 Wenzler

FOREIGN PATENT DOCUMENTS

| DE | 37 29 513 A1 | 3/1988 |
| DE | 41 20 329 A1 | 1/1992 |
| DE | 44 24 659 A1 | 1/1996 |
| DE | 20 2004 015 990 U1 | 12/2004 |
| DE | 202008006005 | 8/2008 |

* cited by examiner

*Primary Examiner* — Ryan Severson
*Assistant Examiner* — Ashley Cronin
(74) *Attorney, Agent, or Firm* — McGlew and Tuttle, P.C.

(57) ABSTRACT

A surgical instrument is provided with a gripping part arranged in a stationary manner on a tubular guide housing having a guide hole and with an actuating lever, which is pivotably mounted thereon and which is in functional connection via a lever arm with a plunger. The plunger is axially shiftable in a mounting housing, via which a tool can be actuated. The plunger has, in its end area located adjacent to the lever arm, a circumferential, radially expanded pushbutton, via which the plunger is guided axially adjustably against the spring force of an axial compression spring in the guide hole of the guide housing. The mounting housing is provided with a ring shoulder for axial fixation in the guide hole of the guide housing.

17 Claims, 4 Drawing Sheets

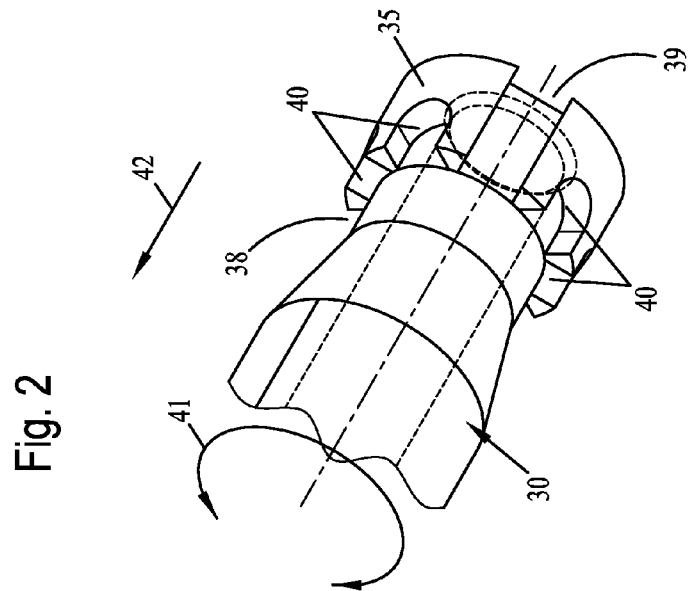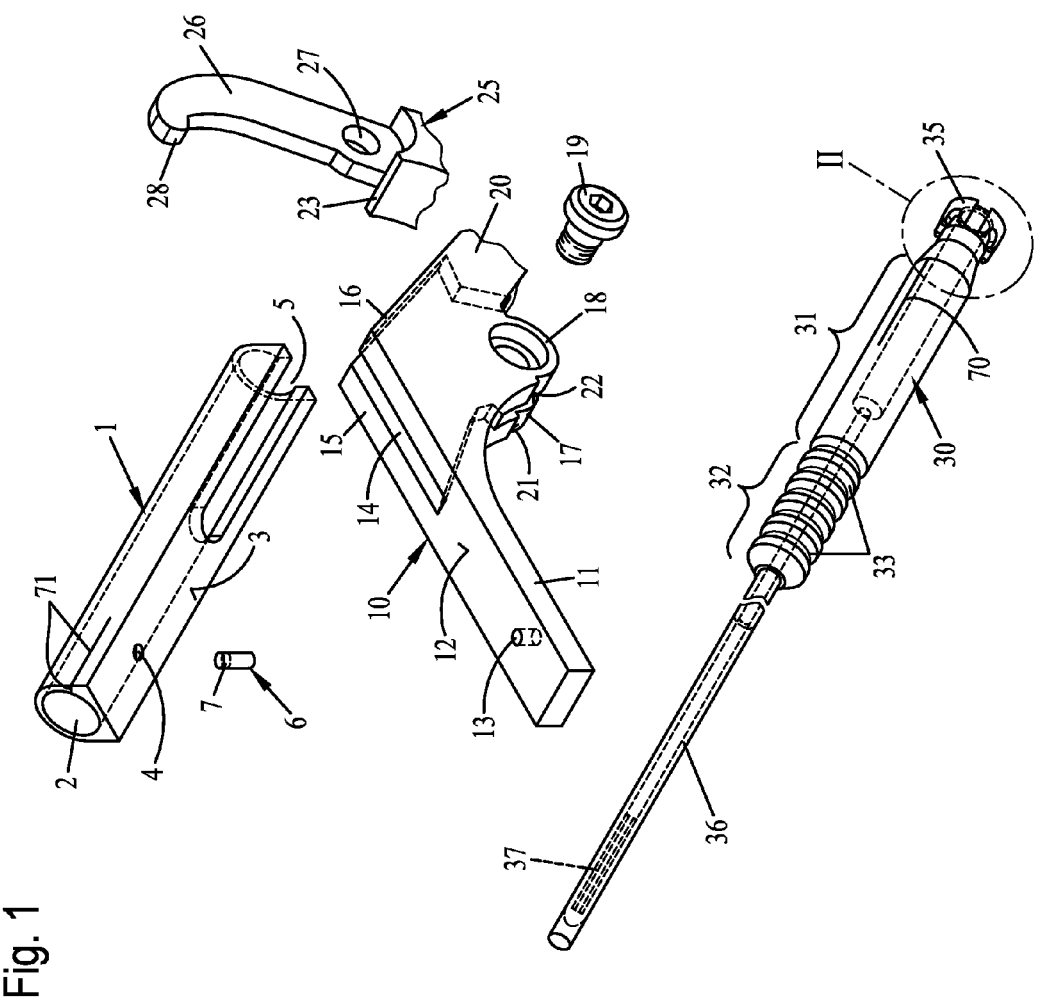

SURGICAL INSTRUMENT

CROSS REFERENCE TO RELATED APPLICATIONS

This application claims the benefit of priority under 35 U.S.C. §119 of German Patent Application DE 20 2008 015 151.1 filed Nov. 14, 2009, the entire contents of which are incorporated herein by reference.

FIELD OF THE INVENTION

The present invention pertains to a surgical instrument with a gripping part arranged stationarily on a tubular guide housing having a guide hole and with an actuating lever, which is mounted pivotably thereon and which is in functional connection via a lever arm with a plunger, which is axially adjustable in a mounting housing and via which a tool can be actuated, wherein the plunger has, in its end area located adjacent to the lever arm, a circumferential, radially expanding pushbutton, via which the plunger is guided in an axially adjustable manner against the spring force of an axial compression spring in the guide hole of the guide housing, and wherein the mounting housing is provided with a ring shoulder for axial fixation in the guide hole of the guide housing.

BACKGROUND OF THE INVENTION

Surgical instruments of the type of this class have been known for a quite some time. They have different names for different intended uses. For example, bone punches, rongeurs as well as endoscopic punches can be mentioned here, and this listing shall not be considered to be limiting. It is common to these instruments that they have a gripping part with a kind of guide housing, in which a tool is mounted replaceably. This tool is activated by actuating an actuating lever, and this tool may be, for example, a punching tool, a gripping tool or even a kind of scissors.

Reference shall be made for this, for example, to DE 20 2008 006 005 U1. The subject of this German utility model is a so-called bone punch. Such a bone punch differs, for example, from an endoscopic punch by the concrete embodiment of the tool proper. A guide housing, which is rigidly in connection with a gripping part, is provided in the prior-art bone punch. This gripping part forms a rigid gripping element and has an actuating lever, which is pivotable in relation to the gripping part or gripping element. This actuating element forms a lever section, by which a plunger of the punching tool, which said plunger is mounted in the guide housing and is provided with a pushbutton, is adjustable axially during the actuation of the actuating lever. A punch slide, which can be adjusted by the plunger along a punching bar from a retracted starting position into an advanced end position against the spring force of an axial compression spring, is in connection with said plunger. This axial compression spring is arranged in the area of the plunger between the pushbutton and a mounting housing of the plunger, so that the plunger is held via the pushbutton thereof in its retracted starting position by this axial compression spring. Furthermore, the mounting housing is provided with a ring shoulder in its end area located in the guide housing. In the state in which the mounting housing is mounted in the guide housing, the mounting housing is held in the guide housing in an axially stationary manner via this ring shoulder and a locking element protruding into a guide hole of the guide housing, which said guide hole receives the mounting housing.

This locking element can be shifted from a locking position, which fixes the mounting housing and hence the entire punching tool and protrudes into the guide housing, into a pivoted position releasing the mounting housing or the ring shoulder thereof in the actuation direction. This surgical instrument, called a bone punch, has an extremely complicated design in the area of the gripping part because of this locking element. In particular, a plurality of processing steps are necessary in the area of the gripping part and hence in the area of the guide housing in order to make it possible to insert the locking element. Furthermore, this locking element must be held in its locked position by spring force, so that the mounting housing of the plunger remains stationarily in the guide housing of the gripping part. By actuating this locking element, the latter moves with its locking nose out of the guide hole of the guide housing, so that the entire punching tool with its mounting housing can be removed from the gripping part or the guide housing to the front. Furthermore, this construction has the risk in case of inexperienced handling that the locking element is accidentally actuated and the mounting housing and hence the punching tool proper will unintentionally slip out of the guide housing during use.

It shall be mentioned here once again that, for example, scissors or a gripper or the like may also be provided as the tool instead of the punching slide or the punching tool at the free end of the "punching bar."

SUMMARY OF THE INVENTION

Based on the known state of the art, the basic object of the present invention is to provide a surgical instrument which is simplified in terms of the "locking" of the mounting housing in the guide hole of the guide housing that secure fixation of the mounting housing in the guide housing is guaranteed along with simple handling and low manufacturing costs.

The object is accomplished according to the present invention, together with other features of the combination, by a radially inwardly projecting, pin-like stop being provided in the guide hole of the guide housing and by the ring shoulder having on its circumference an axial groove, which extends from the free end of the ring shoulder into the at least partially circumferential ring groove axially defining the ring shoulder and by the positioning of a section of the stop extending into the guide hole and the dimensions of the axial groove being coordinated such that the ring shoulder with its axial groove can be pushed beyond said section into the guide hole and can be axially locked by said section of the stop in the guide hole after a rotation about the axis of the guide hole.

A surgical instrument that can be manufactured simply and at a low cost is made possible by the embodiment according to the present invention, especially in terms of the fixation of the mounting housing with the plunger thereof in the guide hole of the guide housing of the gripping part. Provisions are made for this for the locking to be designed in the manner of a "bayonet catch." A stop is correspondingly provided, which protrudes into the guide hole of the guide housing. Corresponding to the arrangement and the length of the section protruding into the guide hole, the mounting housing provided with the ring shoulder in the end area has an axial groove in the area of said ring shoulder, and said axial groove can be pushed "over" the pin-like stop. This ring shoulder opens into a circumferential or at least partially circumferential ring shoulder, so that a kind of free space, which may be limited in the circumferential direction or extends completely over the circumference, is obtained behind the ring shoulder. Thus, secure locking of the mounting housing in the guide housing and the guide hole thereof is brought about by simply pushing in the mounting housing with its ring shoulder in a corresponding angular alignment of the axial groove thereof and subsequent rotation of the mounting housing in the guide housing. Extremely simple manufacture is thus guaranteed by this axial groove and the stop, which is designed, for example, as a stop pin, because no additional movable parts, which would possibly have to be held by spring force in their locked positions, are present. In addition, accidental detachment of this type of connection is prevented with certainty, because the mounting housing would have to be rotated for this in the guide housing. However, such a relative rotation of the mounting housing in the guide housing can take place only by deliberate manual "actuation." However, since the hand of a person actuating the actuating lever has a great distance from the mounting housing during use, such an unintended relative rotation cannot be brought about without the second hand of the person being used for assistance. Furthermore, the axial compression spring is maintained under prestress by the retracted starting position of the plunger, so that a certain moment of friction is generated between the ring shoulder and the stop, whereby an especially automatic relative rotation between the mounting housing and the guide housing is ruled out.

Thus, provisions may be made for the ring shoulder to have at least one locking depression towards the ring groove, with which the section of the stop (which protrudes into the guide hole of the guide housing) can be stationarily meshed to fix the relative angular position of the mounting housing in relation to the guide housing and hence to the gripping part. It is ensured by this locking depression that the mounting housing cannot rotate under any circumstances any longer in the guide housing after the locking depression has been locked. Due to this embodiment, the mounting housing must at first be pressed somewhat into the guide housing for removal in order to make it possible to bring about a relative rotation between the mounting housing and the guide housing. This positive-locking meshing of the locking depression with the stop thus leads to added security.

A plurality of locking depressions, which are directed towards the ring shoulder and are distributed uniformly over the circumference, may also be provided in the ring shoulder. The section of the stop that protrudes into the guide hole of the guide housing can be caused to stationarily mesh with these locking depressions to set different relative angular positions of the mounting housing in relation to the guide housing and hence to the gripping part. In particular, the tool proper, which is arranged at the end of a tool part and which may comprise a punch slide of scissors or even a gripper, may be set in a fixed manner in different angular alignments in relation to the gripping part. This is especially advantageous for handling for different intended uses.

Furthermore, provisions may be made for the lever arm of the actuating lever to hold the axial compression spring of the plunger under prestress and for the ring shoulder to be maintained meshed with the section of the stop with one of its locking depressions by the prestressed axial compression spring. On the one hand, the mobile actuating lever is held by this embodiment in its starting position via its lever arm, and, on the other hand, positive-locking meshing of the section of the stop with one of the locking depressions is secured.

Furthermore, provisions may be made for the mounting housing of the plunger to axially outwardly project over the guide housing in the mounted position of the mounting housing in the guide hole of the guide housing and for the mounting housing to have a mark in its part projecting from the guide housing, which mark can be caused to coincide with a mark of the guide housing by rotating the mounting housing in relation to the guide housing, and for the axial groove of the ring shoulder and the section of the stop (which protrudes into the guide hole) to be aligned for mounting or removing the mounting housing in or from the guide housing in case the two marks coincide. In particular, handling is considerably simplified by these marks, which are clearly recognizable from the outside, for the mounting and removal of the mounting housing in the guide housing. Only the two marks must be caused to coincide for this.

An exemplary embodiment of the present invention will be explained in more detail below on the basis of the drawings. The present invention is not limited to the endoscopic punch described only as an example below, but it may also be used in other surgical instruments of a similar shape, such as those mentioned as nonlimiting examples in the introduction to the specification. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a perspective exploded view of a surgical instrument designed as an example as an endoscopic punch with a guide housing, a gripping part, an actuating lever and a mounting housing;

FIG. 2 is an enlarged detail view II of the mounting housing from FIG. 1 in the area of its ring shoulder;

DESCRIPTION OF THE PREFERRED EMBODIMENTS

Figure 3:
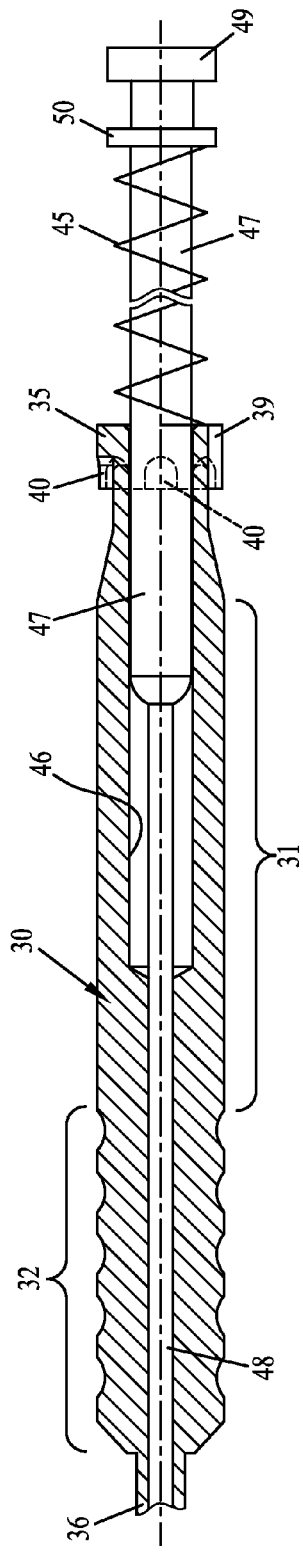
FIG. 3 is a vertical sectional view through the mounting housing together with an inserted plunger as well as an axial compression spring.

Referring to the drawings in particular, FIG. 1 shows a partial perspective exploded view of some components of a surgical instrument according to the present invention, which is designed as a so-called endoscopic punch in the exemplary embodiment being shown. This punch comprises a guide housing 1, which has a through guide hole 2. Further, it can be recognized that the guide housing 1 has on the underside a seating surface 3, in the left front area of which a through hole 4 is provided.

In its end area located opposite the through hole 4, the seating surface 3 is provided with an opening 5, which is open to the "rear" to the right end area of the guide housing 1. This opening 5 extends over about half the axial length of the guide housing 1 in this exemplary embodiment.

Furthermore, a stop pin 6, which can be passed through the through hole 4 and protrudes into the guide hole 2 with an upper section 7 in the mounted state, can be recognized in FIG. 1.

Furthermore, FIG. 1 shows a partial perspective view of a gripping part 10, which forms a mounting section 11. This mounting section 11 has a flat upper support surface 12, on which the guide housing 1 with its lower seating surface 3 can be placed flatly. This support surface 12 is provided in the front end area with a blind hole 13, into which the stop pin 12 can be fittingly inserted such that it "projects" upwardly towards the guide housing 1. This stop pin 6 can be fixed in the blind hole 13, for example, by a pressed connection, bonded connection or also by a soldered connected.

In its end area located opposite the mounting section 11, gripping part 10 has a mounting chamber 14, which is defined laterally by two side walls 15 and 16. This mounting chamber 14 extends downwardly together with the side walls 15 and 16, beginning from the flat support surface 12 and forms two bearing eyes 17 and 18. These bearing eyes 17 and 18 are used, as this is sufficiently known from the state of the art, to mount a bearing bolt 19. In a rearward extension to the two side walls 15 and 16, a stationary gripping element 20, which is shown only partially in FIG. 1, joins downwardly. The mounting chamber 14 is also limited downwardly in the area of this gripping element 20.

As is likewise shown only partially in FIG. 1, an actuating lever 25 with an upwardly projecting lever arm 26 can be inserted into this mounting chamber 14. For rotatable mounting in the mounting chamber 14 via the bearing bolt 19, the actuating lever 25 has a corresponding bearing bore in the lower end area of its lever arm 26. Lever arm 26 is provided with a pressing pin 28 projecting towards the mounting section 11 in the upper end area.

Furthermore, FIG. 1 shows in a foreshortened view a mounting housing 30, which forms a guide section 31. The mounting housing 30 can be inserted with this guide section 31 into the guide hole 2 of the guide housing 1 at least partially from the "front" in the axial direction. Guide section 31 is adjoined by a handling section 32, which is provided with a plurality of circumferential gripping grooves 33 in this exemplary embodiment.

In its rearward rear end area, this mounting housing 30 forms a ring shoulder 35, which is shown enlarged in FIG. 2. In its end area located opposite this ring shoulder 35, a guide tube 36, used for the axially shiftable mounting of a push rod not shown in more detail in FIG. 1, is arranged on the mounting housing 30. In the front outer end area this guide tube 36 has a bearing section 37, which is used to adjustably mount the tool proper, which may be a punch slide (not shown in the drawing) in the exemplary embodiment of the endoscopic punch being shown. Such a punch slide will be described later in connection with FIG. 5.

As is apparent from FIG. 2, the ring shoulder 35 of the mounting housing 30 is axially limited in the axial direction by a ring groove 38, which extends circumferentially in the exemplary embodiment being shown. Furthermore, FIG. 2 shows that the ring shoulder 35 is provided with an axial groove 39 extending over the entire axial length of said ring shoulder. The ring groove 38 may also be designed such that it is defined in the circumferential direction beginning from the axial groove 39. Furthermore, ring shoulder 35 forms a plurality of locking depressions 40 opening into the ring groove 38. With these locking depressions 40, the ring shoulder 35 can be caused to mesh with section 7 of the stop pin 6 from FIG. 1, which said section protrudes into guide hole 2, in the correctly mounted state in a positive-locking manner. These locking depressions 40 do not necessarily have to be provided.

To mount the mounting housing 30 in the guide hole 2 of guide housing 1, the mounting housing 30 with its ring shoulder 35 can be pushed into the guide hole 2. During pushing in, the axial groove 39 can be pushed over section 7 of the stop pin 6 protruding into the guide hole 2 by a corresponding angular alignment of the mounting housing 30 in relation to the guide housing 1 until the stop pin 6 comes to lie in the area of the ring groove 38. By rotating the mounting housing 30 together with the ring shoulder 35 in one of the directions indicated by double arrow 41, one of the locking depressions 40 can now be caused to overlap with section 7. Mounting housing 30 is now pressed by spring force in the direction of arrow 42, so that section 7 of the stop pin 6 will mesh with one of the locking depressions 40 in a positive-licking manner. If no locking depressions 40 are provided, the ring shoulder 35 itself is pressed by the spring force against section 7 of the stop pin 6, so that frictional engagement is brought about between these components and the mounting housing 30 cannot readily rotate by itself in guide housing 1.

The simplify the mounting and removal of the mounting housing 30 in and from the guide housing 1, the mounting housing 30 may be provided with a mark 70, which is visible from the outside and which can be aligned with a mark 71 of the guide housing 1, which said mark 71 is likewise visible from the outside. These two marks 70 and 71 are shown as examples in FIG. 1. Alignment of axial groove 30 with section 7 of the stop pin 6 is simplified by these marks 70 and 71.

The spring force necessary for the positive-locking engagement of section 7 of the stop pin 6 with one of the locking depressions 40 is brought about by an axial compression spring 45 in this exemplary embodiment, as this is schematically shown as an example in FIG. 3. FIG. 3 correspondingly shows for this the mounting housing 30 with its guide section 31 as well as with its handling section 32 in a vertical section. Furthermore, it can be recognized from FIG. 3 that a plunger 47 is inserted axially adjustably in mounting housing 30 or in a section of a guide hole 46 of mounting housing 30. This plunger is joined by the above-mentioned push rod 48, which has a radially tapered design compared to plunger 47. This push rod 48 passes through the guide tube 36, as this is indicated in FIG. 3.

In its retracted position, plunger 47 axially projects from the guide housing 30 and hence also from the ring shoulder 35. In its free end area, plunger 47 may have, for example, a pushbutton 49, via which the plunger 47 is in functional connection with the pressing pin 28 of lever arm 26 of actuating lever 25 from FIG. 1 in the mounted state.

Furthermore, a radially expanded support ring 50 may be provided with an axial offset in relation to this pushbutton 49 towards the ring shoulder 35. The axial compression spring 45 is received prestressed between this support ring 50 and the ring shoulder 35 of mounting housing 30, so that plunger 47 together with the push rod is held in its retracted position shown in FIG. 3. The position of this starting position is determined by the functional connection between the pressing pin 28 of the actuating lever 25 and pushbutton 49, as this can be recognized especially from FIG. 7. Furthermore, the locking depressions 40 as well as the axial groove 39 of the ring shoulder 35 can also be recognized in FIG. 3.

Figure 4:
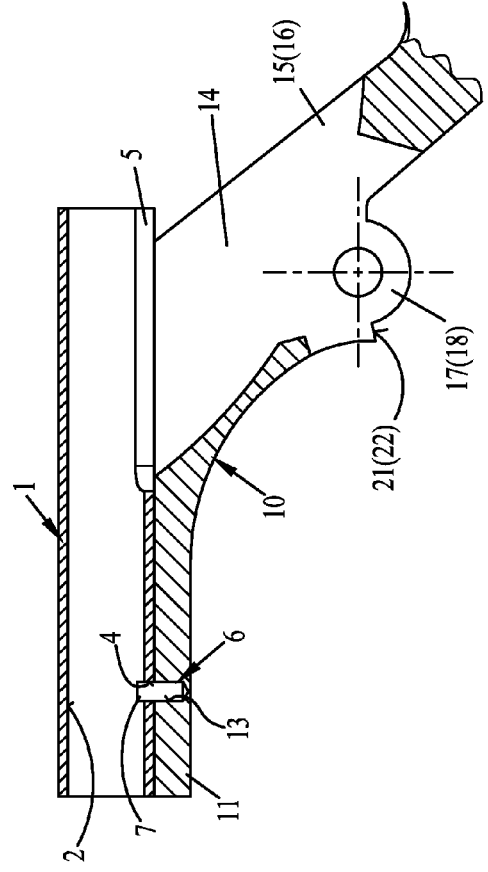
FIG. 4 is a partial vertical sectional view through a gripping part with the guide housing attached.

FIG. 4 shows a partial vertical section of gripping part 10, to which the guide housing 1 is attached. It can be recognized that stop pin 6 is inserted into the blind hole 13 of the mounting section 11 of gripping part 10. Stop pin 6 passes through the through hole 4 of guide housing 1 with its section 7, so that stop pin 6 protrudes with this section into the guide hole 2 of guide housing 1.

In this state, in which guide housing 1 is attached to the mounting section 11, opening 5 of the guide housing 1 extends over the entire axial length of mounting chamber 14 of gripping part 10. Furthermore, it can be recognized from FIG. 3 that the bearing eyes 17 and 18 of the two side walls 15 and 16 form a radially projecting adjusting stop 21 and 22, respectively, as this can also be recognized from FIG. 1. In cooperation with a corresponding stop web 23 of the actuating lever 25, (FIG. 1), the retracted starting position of both the actuating lever 25 and of plunger 47 is defined by the two adjusting stops 21 and 22. Only side wall 15 and the bearing eye 17 as well as stop 21 are visible in FIG. 4 because of the direction of the section.

Figure 5:
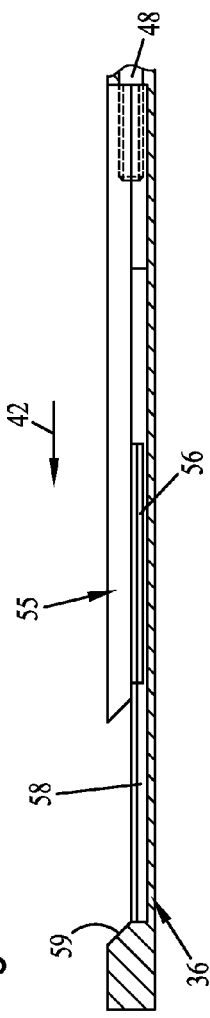
FIG. 5 is a partial vertical sectional view of the tool of the surgical instrument, which tool is designed, for example, as a punching tool.

FIG. 5 shows a partial vertical section of guide tube 36 in the area of its bearing section 37, in which the above-mentioned punch slide 55 is mounted. It can be recognized that push rod 48 is screwed into the punch slide 55. FIG. 5 shows a retracted axial position of punch slide 55 in the vertical section shown. This punch slide 55 is mounted axially adjustably in the bearing section via a T-piece made integrally in one piece with the punch slide 55 and via a correspondingly shaped T-groove 57 of bearing section 37. If punch slide 55 is now moved, by actuating the actuating lever 25 from FIG. 1 via the push rod 48, in the direction of arrow 42, punch slide 55 with its punching edge 58 provided at the end reaches a stop 59 of the guide tube 36, so that tissue samples can be taken in a simple manner. Another "tool," for example, in the form of scissors, a gripper or the like, which can be actuated by the push rod 48, may also be provided in the end area of guide tube 36 instead of such a punch slide 55. It is also possible to provide, as in the case of, e.g., bone punches, a guide bar, on which a punch slide is mounted in an axially displaceable manner, instead of guide tube 36.

Figures 6, 6A:
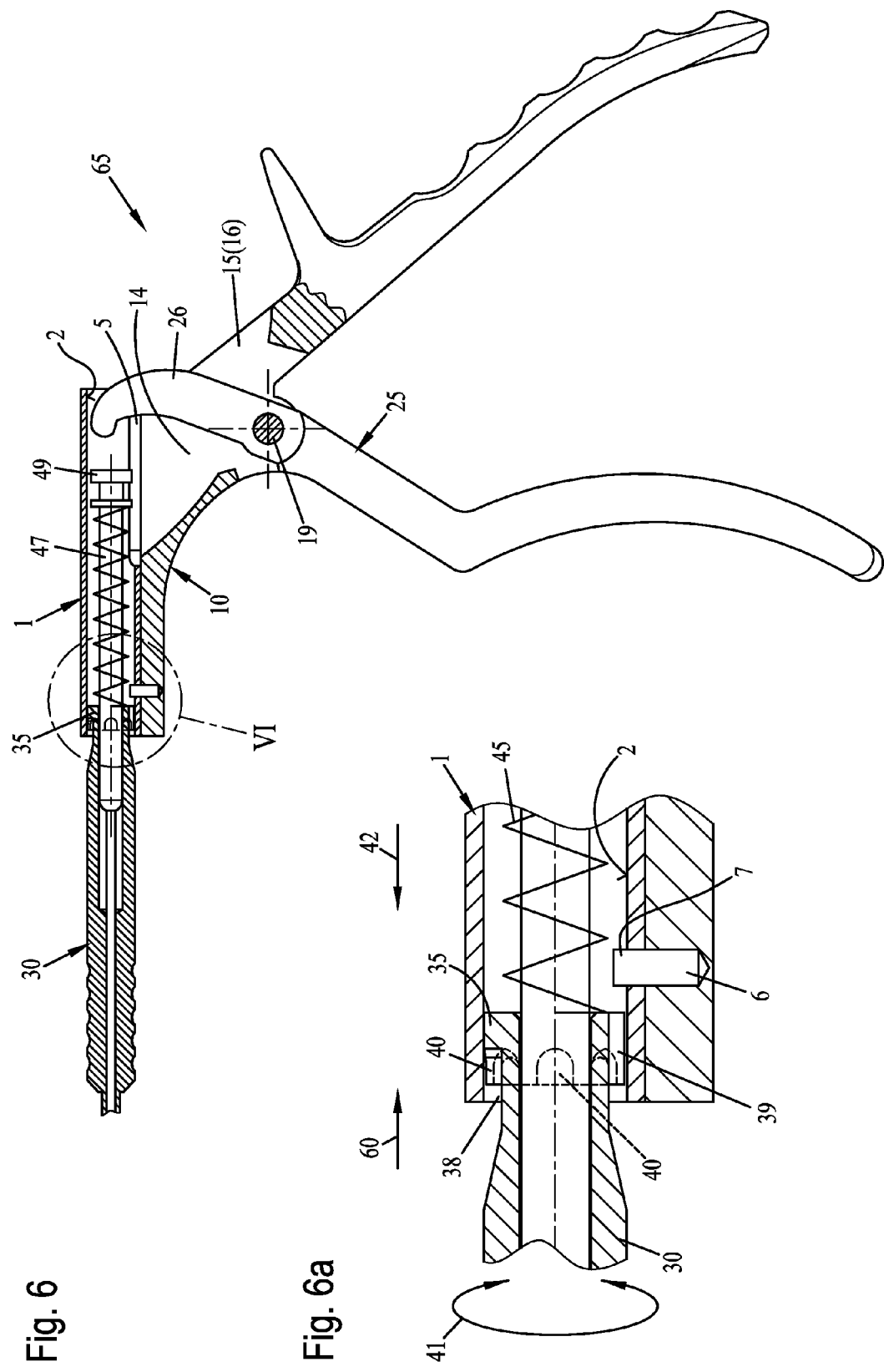
FIG. 6 is the gripping part with the guide housing attached as well as the actuating lever inserted and the guide housing attached with the plunger.
FIG. 6a is an enlarged detail view VI from FIG. 6.

In this exemplary embodiment the above-described components form an endoscopic punch 65 in the completely mounted state, as this is shown in a partial vertical section in FIG. 6. It can be recognized that the actuating lever 25 is inserted into the mounting chamber 14 of gripping part 10 and is mounted rotatably in the side walls 15 and 16 by means of bearing bolt 19. Lever arm 26 protrudes into the guide hole 2 of guide housing 1 through opening 5. In the view shown in FIG. 6, mounting housing 30 is inserted with its ring shoulder 35 into guide hole 2 of the guide housing. Plunger 47 is guided in guide hole 2 with a clearance especially by its pushbutton 49.

FIG. 6a shows for this an enlarged detail VI from FIG. 6. It can be recognized that the axial groove 39 of ring shoulder 35 is directed towards section 7 of the stop pin 6, which said section protrudes into guide housing 2. By displacing the mounting housing 30 more in the direction of arrow 60, the ring shoulder 35 with its axial groove 39 is now pushed over section 7 of stop pin 6 until the ring groove 38 of mounting housing 30 comes to lie in the area of this section 7. As is described in connection with FIG. 2, mounting housing 30 can be subsequently rotated in one of the directions indicated by double arrow 41, so that section 7 will overlap one of the locking depressions 40 of ring shoulder 35. Due to a subsequent resetting motion in the direction of arrow 42, which is brought about by the spring force of the axial compression spring 45, section 7 of stop pin 6 will become stationarily meshed with one of the locking depressions 40 of ring shoulder 35. Such a meshing can be seen especially in FIGS. 7 and 7a.

Figures 7, 7A:
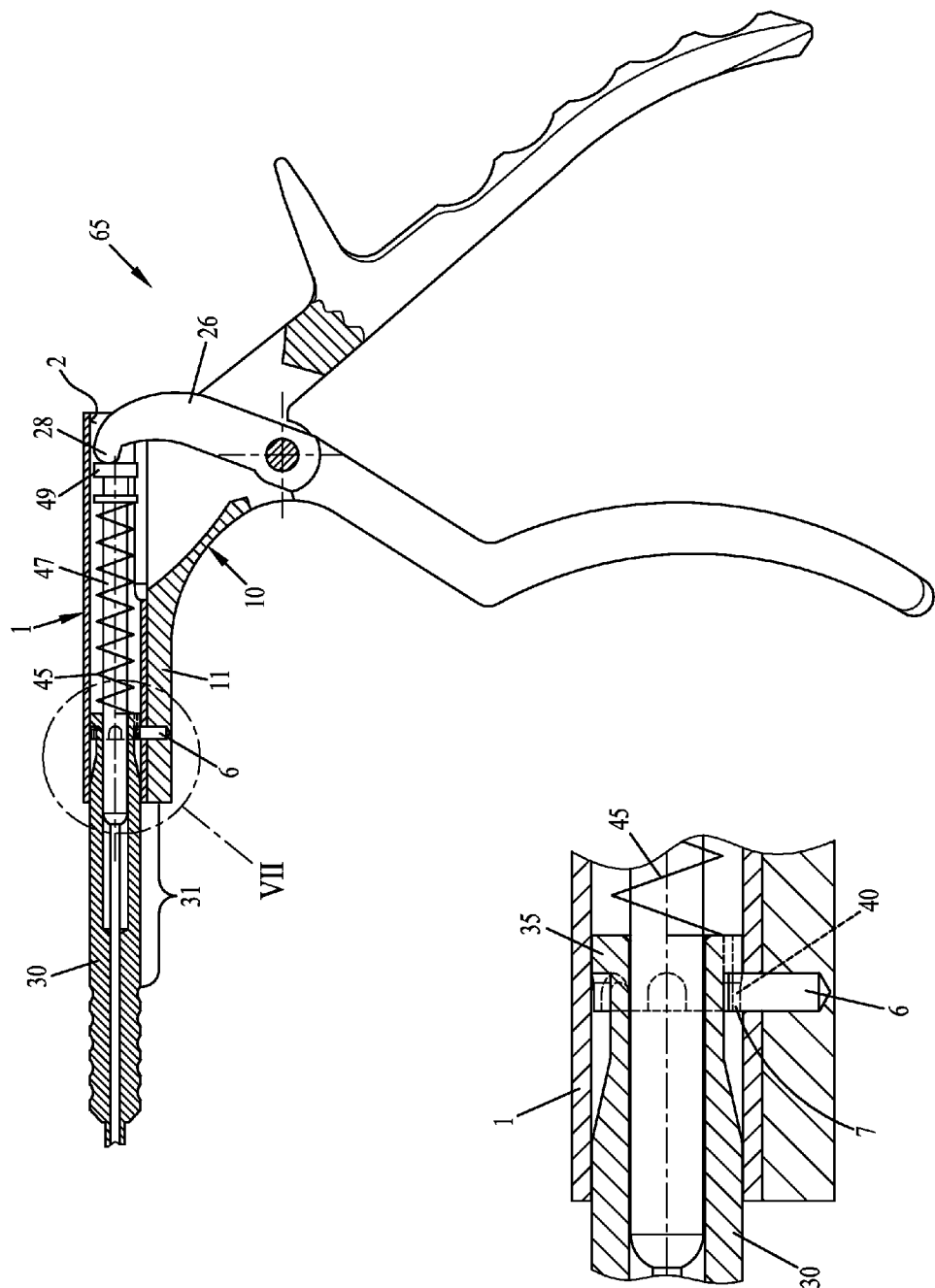
FIG. 7 is in a partial vertical sectional view similar to FIG. 6, in which the mounting housing is inserted stationarily into the guide housing of the gripping part.
FIG. 7a is an enlarged detail view VII from FIG. 7.

It can be recognized from FIG. 7, which corresponds to the view in FIG. 6 concerning the partial vertical section, that pushbutton 49 and pressing pin 28 of the lever arm 26 are in functional connection with one another. FIG. 7 shows a retracted axial position of plunger 47 in the guide housing 1. The mounting housing 30 is seated with part of its guide section 31 in the guide hole 2 of guide housing 1. The positioning of stop pin 6 as well as the length of the part of plunger 47 projecting from the mounting housing 30 and protruding into guide hole 2 are selected now to be such that the axial compression spring 45 is under prestress in the position shown in FIG. 7 or retracted axial position of plunger 47. It is thus achieved that section 7 of the stop pin 6 remains stationarily in connection with one of the locking depressions 40 of ring shoulder 35 in a positive-locking manner. This can be recognized from the enlarged view VII in FIG. 7a.

It shall also be mentioned here that guide housing 1 is stationarily attached to the mounting section 11 of gripping part 10 by a soldered connection, welded connection or the like in the exemplary embodiment being shown here.

It can be stated in summary that extremely simple mounting of the mounting housing 30 in the guide housing 1 of the endoscopic punch 65 shown here as an example is made possible by the embodiment according to the present invention of the ring shoulder 35 with its axial groove 39 as well as of the section 7 of the stop pin 6, which said section 7 protrudes into the guide hole 2 of guide housing 1. In particular, extremely cost-effective manufacture is ensured by this simple embodiment, because only a small number of parts are to be manufactured here in a simple manner. Unintentional detachment of this connection is also ruled out.

While specific embodiments of the invention have been described in detail to illustrate the application of the principles of the invention, it will be understood that the invention may be embodied otherwise without departing from such principles.

What is claimed is:

1. A surgical instrument comprising:
   a gripping part;
   a tubular guide housing having a guide hole, said gripping part being arranged stationarily on said tubular guide housing;
   a plunger;
   a mounting housing having a ring shoulder for axial fixation in said guide hole of said guide housing, said ring shoulder having a first groove on a circumference thereof, said first groove forming an axial groove extending, in an axial direction of said mounting housing and said first groove extending from a free end of said ring shoulder and said first groove leading into a second groove, said second groove forming an at least partially circumferential ring groove, said at least partially circumferential ring groove forming an axial boundary of said ring shoulder defining an axial length of said ring shoulder;
   a tool;
   an axial compression spring;
   an actuating lever with a lever arm, said actuating lever being mounted pivotably on said guide housing and in functional connection with said plunger, said plunger being axially shiftable in said mounting housing via said lever arm and via which said tool can be actuated, wherein said plunger has an end area located adjacent to said lever arm with a circumferential radially expanded pushbutton, said pushbutton for guiding said plunger axially shiftably in said guide hole of said guide housing against a spring force of said axial compression spring;

a stop pin forming a stop section, said stop section projecting stationarily, radially inwardly in said guide hole, and dimensions of said axial groove are coordinated with dimensions of said stop section of said stop pin such that said axial groove of said ring shoulder can be pushed beyond said stop section into said guide hole and can be axially locked in said guide hole by said stop section by a rotation about an axis of said guide hole, said ring shoulder having at least one locking depression extending towards and leading into said ring groove, said locking depression for causing said stop section to engage in a stationary manner to fix a relative angular position of said mounting housing in relation to said guide housing and to said gripping part.

2. A surgical instrument in accordance with claim 1, wherein:
said lever arm of said actuating lever maintains said axial compression spring of said plunger under prestress; and
said ring shoulder is kept engaged with said stop section with said locking depression by said prestressed axial compression spring.

3. A surgical instrument in accordance with claim 1, wherein:
said mounting housing axially projects over said guide housing to an outside in a mounted position of said mounting housing in said guide hole of said guide housing;
said mounting housing has a mounting housing mark in a part projecting from said guide housing;
said guide housing has a guide housing mark;
said mounting housing mark may be caused to coincide with said guide housing mark by rotating said mounting housing in relation to said guide housing; and
said axial groove of said ring shoulder and said stop section are aligned with one another in case of alignment of said guide housing mark and said mounting housing mark for mounting and removal of said mounting housing on and from said guide housing.

4. A surgical instrument in accordance with claim 1, wherein said lever arm engages said pushbutton.

5. A surgical instrument in accordance with claim 1, wherein said stop pin engages said gripping part.

6. A surgical instrument comprising:
a gripping part;
a tubular guide housing having a guide hole, said gripping part being arranged stationarily on said tubular guide housing;
a plunger;
a mounting housing having a ring shoulder for axial fixation in said guide hole of said guide housing, said ring shoulder having a first groove on a circumference thereof, said first groove forming an axial groove extending, in an axial direction of said mounting housing and said first groove extending from a free end of said ring shoulder and said first groove leading into a second groove, said second groove forming an at least partially circumferential ring groove, said at least partially circumferential ring groove forming an axial boundary of said ring shoulder defining an axial length of said ring shoulder;
a tool;
an axial compression spring;
an actuating lever with a lever arm, said actuating lever being mounted pivotably on said guide housing and in functional connection with said plunger, said plunger being axially shiftable in said mounting housing via said lever arm and via which said tool can be actuated, wherein said plunger has an end area located adjacent to said lever arm with a circumferential radially expanded pushbutton, said pushbutton for guiding said plunger axially shiftably in said guide hole of said guide housing against a spring force of said axial compression spring;
a stop pin forming a stop section, said stop section projecting stationarily, radially inwardly in said guide hole, and dimensions of said axial groove are coordinated with dimensions of said stop section of said stop pin such that said axial groove of said ring shoulder can be pushed beyond said stop section into said guide hole and can be axially locked in said guide hole by said stop section by a rotation about an axis of said guide hole, wherein said ring shoulder has a plurality of locking depressions, each of said locking depressions extending towards and leading into said ring groove, said locking depressions being arranged uniformly over a circumference to engage with said stop section in a stationary manner to set one of different relative angular positions of said mounting housing in relation to said guide housing and to said gripping part.

7. A surgical instrument in accordance with claim 6, wherein:
said lever arm of said actuating lever maintains said axial compression spring of said plunger under prestress; and
said ring shoulder is kept engaged with said stop section with one of said locking depressions by said prestressed axial compression spring.

8. A surgical instrument comprising:
a gripping part;
a tubular guide housing having a guide hole, said gripping part being fixed to said tubular guide housing;
a plunger comprising a circumferential radially expanded pushbutton at an end thereof;
amounting housing comprising a ring shoulder and a second groove, said ring shoulder having an outer circumferential ring shoulder surface, said outer circumferential ring shoulder surface defining a first groove, said first groove extending in an axial direction of said mounting housing, one end of said first groove being at or adjacent to a free end of said ring shoulder and another end of said first groove being at or adjacent to said second groove, said second groove forming an at least partially circumferential ring groove;
a tool;
an axial compression spring, one end of said axial compression spring engaging said ring shoulder;
an actuating lever comprising a lever arm, said actuating lever being mounted pivotably on said gripping part and said actuating lever being operably connected to said plunger, wherein said plunger moves in said mounting housing in the axial direction and said tool moves in the axial direction based on movement of said actuating lever, at least a portion of said lever arm being located adjacent to said pushbutton, said pushbutton guiding said plunger in the axial direction in said guide hole of guide housing based on movement of said actuating lever;
a stop pin extending in a radially inward direction with respect to the axial direction, at least a portion of said stop pin being located in said guide hole, wherein a dimension of said axial groove is greater than a dimension of said at least said portion of said stop pin such that said axial groove of said ring shoulder is pushed beyond said at least said portion of said stop pin into said guide hole and said ring shoulder is axially locked in said guide hole by said at least said portion of said stop pin by a rotation about an axis of said guide hole, wherein said ring shoulder is fixed in said guide hole via said stop pin, said ring shoulder having at least one locking depression extending in the axial direction towards said ring groove, said at least one locking depression leading into said ring groove, said locking depression receiving at least a portion of said at least said portion of said stop pin, wherein said at least said portion of said stop pin and said at least one locking depression fix a relative angular position of said mounting housing in relation to said guide housing and to said gripping part.

9. A surgical instrument in accordance with claim 8, wherein:
said lever arm of said actuating lever maintains axial compression spring of said plunger under prestress; and
said ring shoulder is kept engaged with said at least said portion of said stop pin with said locking depression by said prestressed axial compression spring.

10. A surgical instrument in accordance with claim 8, wherein:
said mounting housing axially projects over said guide housing to an outside in a mounted position of said mounting housing in said guide hole of said guide housing;
said mounting housing has a mounting housing mark in a part projecting from said guide housing, said mounting housing mark corresponding to a position of said first groove;
said guide housing has a guide housing mark, said guide housing mark corresponding to a position of said at least said portion of said stop pin;
said first groove is aligned with said at least said portion of said stop pin with said mounting housing mark coinciding with said guide housing mark.

11. A surgical instrument in accordance with claim 8, wherein said lever arm engages said pushbutton.

12. A surgical instrument in accordance with claim 8, wherein said stop pin engages said gripping part.

13. A surgical instrument in accordance with claim 8, wherein said gripping part comprises a planar mounting portion, at least a portion of said tubular guide housing engaging said planar mounting portion, said planar mounting portion comprising a planar mounting portion stop pin receiving hole, said tubular guide housing comprising a housing stop pin receiving hole, said housing stop pin receiving hole being aligned with said planar mounting portion stop pin receiving hole, one end of said stop engaging said planar mounting portion, said stop pin extending through said housing stop pin receiving hole and said planar mounting portion stop pin receiving hole.

14. A surgical instrument comprising:
a gripping part;
a tubular guide housing having a guide hole, said gripping part being fixed to said tubular guide housing;
a plunger comprising a circumferential radially expanded pushbutton at an end thereof;
amounting housing comprising a ring shoulder and a second groove, said ring shoulder having an outer circumferential ring shoulder surface, said outer circumferential ring shoulder surface defining a first groove, said first groove extending in an axial direction of said mounting housing, one end of said first groove being at or adjacent to a free end of said ring shoulder and another end of said first groove being at or adjacent to said second groove, said second groove forming an at least partially circumferential ring groove;
a tool;
an axial compression spring, one end of said axial compression spring engaging said ring shoulder;
an actuating lever comprising a lever arm, said actuating lever being mounted pivotably on said gripping part and said actuating lever being operably connected to said plunger, wherein said plunger moves in said mounting housing in the axial direction and said tool moves in the axial direction based on movement of said actuating lever, at least a portion of said lever arm being located adjacent to said pushbutton, said pushbutton guiding said plunger in the axial direction in said guide hole of guide housing based on movement of said actuating lever;
a stop pin extending in a radially inward direction with respect to the axial direction, at least a portion of said stop pin being located in said guide hole, wherein a dimension of said axial groove is greater than a dimension of said at least said portion of said stop pin such that said axial groove of said ring shoulder is pushed beyond said at least said portion of said stop pin into said guide hole and said ring shoulder is axially locked in said guide hole by said at least said portion of said stop pin by a rotation about an axis of said guide hole, wherein said ring shoulder is fixed in said guide hole via said stop pin, wherein said ring shoulder has a plurality of locking depressions, each of said locking depressions extending in the axial direction towards said ring groove and each of said locking depressions leading into said ring groove, said locking depressions being distributed uniformly over a circumference of said ring shoulder, each of said locking depressions defining a different relative angular position of said mounting housing in relation to said guide housing and said gripping part, one of said locking depressions receiving at least a portion of said at least said portion of said stop pin, said at least one of said locking depressions and said stop pin fixing said mounting housing relative to said guide housing and said gripping part.

15. A surgical instrument in accordance with claim 14, wherein:
said lever arm of said actuating lever maintains axial compression spring of said plunger under prestress; and
said ring shoulder is kept engaged with said at least said portion of said stop pin with one of said locking depressions by said prestressed axial compression spring.

16. A surgical instrument comprising:
a gripping part;
a tubular guide housing having a guide hole, said gripping part being fixed to said tubular guide housing;
a plunger comprising a circumferential radially expanded pushbutton at an end thereof;
a mounting housing comprising a ring shoulder and an at least partially circumferential ring groove, said ring shoulder having an outer circumferential ring shoulder surface, said outer circumferential ring shoulder surface defining a first groove, said first groove extending in an axial direction of said mounting housing, one end of said first groove being adjacent to a free end of said ring shoulder and another end of said first groove being adjacent to said at least partially circumferential ring groove, said at least partially circumferential ring groove defining a second groove of said mounting housing;
a tool;
an axial compression spring engaging said ring shoulder;
an actuating lever with a lever arm, said actuating lever being mounted pivotably on said gripping part and said actuating lever being operably connected to said plunger, wherein said plunger moves in said mounting housing in the axial direction and said tool moves in the axial direction based on movement of said actuating lever, at least a portion of said lever arm being located adjacent to said pushbutton, said pushbutton guiding said plunger in the axial direction in said guide hole of guide housing based on movement of said actuating lever;

a stop pin extending in a radially inward direction with respect to the axial direction, at least a portion of said stop pin being located in said guide hole, wherein a dimension of said first groove is greater than a dimension of said at least said portion of said stop pin, at least a portion of said mounting housing being inserted in said guide hole with said ring shoulder in a first position, said first groove being aligned with said at least said portion of said stop pin with said ring shoulder in said first position, said ring shoulder being rotated about an axis of said guide hole to a second position after said at least said portion of said mounting housing is inserted in said guide hole, said first groove being located at a spaced location from said at least said portion of said stop pin in said second position, said ring shoulder engaging said at least said portion of said stop pin with said ring shoulder in said second position, wherein said ring shoulder is fixed in said guide hole via said stop pin with said ring shoulder in said second position, said ring shoulder having a plurality of locking depressions, each of said locking depressions extending in the axial direction towards and leading into said ring groove, said locking depressions being arranged uniformly over a circumference of said ring shoulder, each of said locking depressions defining a different relative angular position of said mounting housing in relation to said guide housing and said gripping part, one of said locking depressions receiving at least a portion of said at least said portion of said stop pin, said at least one of said locking depressions and said stop pin fixing said mounting housing relative to said guide housing and said gripping part.

17. A surgical instrument in accordance with claim 16, wherein said ring shoulder is located on one side of said at least said portion of said stop pin with said ring shoulder in said first position, said ring shoulder being located on another side of said at least said portion of said stop pin with said ring shoulder in said second position.

* * * * *